United States Patent
Jacobi et al.

(10) Patent No.: US 7,887,821 B2
(45) Date of Patent: Feb. 15, 2011

(54) PROCESS FOR PRODUCING AN ALLERGEN EXTRACT

(75) Inventors: Henrik Hugo Jacobi, Charlottenlund (DK); Hans-Henrik Ipsen, Hillrod (DK); Tine Charlotte Beck, Birkerod (DK); Merete Stavnsbjerg, Allerod (DK)

(73) Assignee: Alk-Abello A/S, Horsholm (DK)

( * ) Notice: Subject to any disclaimer, the term of this patent is extended or adjusted under 35 U.S.C. 154(b) by 0 days.

(21) Appl. No.: 12/004,101

(22) Filed: Dec. 20, 2007

(65) Prior Publication Data

US 2009/0162403 A1    Jun. 25, 2009

(51) Int. Cl.
*A61K 39/35* (2006.01)
*A61K 39/36* (2006.01)
*C12N 15/09* (2006.01)

(52) U.S. Cl. .................................... 424/276.1; 435/69.3

(58) Field of Classification Search ........................ None
See application file for complete search history.

(56) References Cited

U.S. PATENT DOCUMENTS 7,579,448 B2 * 8/2009 Lester et al. ................. 530/419
2004/0138424 A1 * 7/2004 Takeda et al. ............ 530/387.1

FOREIGN PATENT DOCUMENTS

| CS | 8803908 | 3/1990 |
| WO | WO-94/06821 | 3/1994 |
| WO | WO-94/09824 | 5/1994 |

OTHER PUBLICATIONS

Mukhopadhyay et al. 'Inclusion bodies and purfication of proteins in biologically active forms.' Adv. Biochem. Eng. 56:61-109, 1997.*
Chowdhury et al. 'Antigenic relationship between four airborne palm pollen grains from Calcutta, India.' Ann. Agric. Environ. Med. 6:53-56, 1999.*
Hauck et al. 'The Manufacture of Allergenic Extracts in North America.' Clin. Rev. Allerg. Immununol. 21:93-110, 2001.*
Asturias et al. 'Tolerance and immunological changes of chemically modified allergen vaccine of Parietaria judaica in accelerated schedules.' Clin. Exp. Immunol. 147:491-496, 2007.*
Pacakova et a., "High-performance separations in isolation and characterization of allergens",*Journal of Chromatography B*, Oct. 10, 1997, vol. 669, No. 1-2, pp. 403-418.
Van Neerven et al., "A double-blind, placebo-controlled birch allergy vaccination study: inhibition of CD23-mediated serum-immunoglobulin E-facilitated allergen presentation", *Clinical and Experimental Allergy*, Mar. 2004, vol. 34, No. 3, pp. 420-428.
Larsen et al., "Therapeutische Allergieimpfung", *Allergologie*, Feb. 2000, vol. 23, No. 2, pp. 92-96.
Cromwell et al., "Transition of recombinant allergens from bench to clinical application" *Methods: A Companion to Methods in Enxymology*, Academic Press, NY, NY, Mar. 2004, vol. 32, No. 3, pp. 300-312.
Kleine-Tebbe et al., "Transition of recombinant allergens from bench to clinical application", *Allergy*, Feb. 2006, vol. 61, No. 2, pp. 181-184.

* cited by examiner

*Primary Examiner*—Nora M Rooney
(74) *Attorney, Agent, or Firm*—Birch, Stewart, Kolasch & Birch, LLP

(57) ABSTRACT

The present invention relates to a process for producing an allergen extract from a biological allergen source material comprising the steps of a) contacting the source material with a liquid extraction agent to produce a allergen extract mixture containing allergens dissolved in a liquid phase and a solid phase consisting of source material residues, b) subjecting the allergen extract mixture to a first separation step to remove the solid phase to produce a crude allergen extract, c) subjecting the crude allergen extract to a low molecular fraction removal step to remove molecules having a molecular size of less than 10 kDa, and d) carrying out step c) until the allergen extract has conductivity of below 2000 µS/cm at 25° C. to obtain a purified allergen extract.

16 Claims, No Drawings

PROCESS FOR PRODUCING AN ALLERGEN EXTRACT

TECHNICAL FIELD

The present invention relates to a process for producing an allergen extract from a biological allergen source material.

BACKGROUND OF THE INVENTION

Allergy is a major health problem in countries where Western lifestyle is adapted. Furthermore, the prevalence of allergic disease is increasing in these countries. Although allergy in general may not be considered a life-threatening disease, asthma annually causes a significant number of deaths. An exceptional prevalence of about 30% in teenagers conveys a substantial loss in quality of life, working days and money, and warrants a classification among major health problems in the Western world.

Allergy is a complex disease. Many factors contribute to the sensitisation event. Among these is the susceptibility of the individual defined by an as yet insufficiently understood interplay between several genes. Another important factor is allergen exposure above certain thresholds. Several environmental factors may be important in the sensitisation process including pollution, childhood infections, parasite infections, intestinal microorganisms, etc. Once an individual is sensitised and the allergic immune response established, the presence of only minute amounts of allergen is efficiently translated into symptoms.

The natural course of allergic disease is usually accompanied by aggravation at two levels. Firstly, a progression of symptoms and disease severity, as well as disease progression, for example from hay fever to asthma. Secondly, dissemination in offending allergens most often occurs resulting in allergic multi-reactivity. Chronic inflammation leads to a general weakening of the mucosal defense mechanisms resulting in unspecific irritation and eventually destruction of the mucosal tissue. Infants may become sensitised primarily to foods, i.e. milk, resulting in eczema or gastrointestinal disorders; however, most often they outgrow these symptoms spontaneously. These infants are at risk of developing inhalation allergy later in their lives.

The most important allergen source are found among the most prevalent particles of a certain size in the air we breathe. These sources are remarkably universal and include grass pollens and house dust mite faecal particles, which together are responsible for approximately 50% of all allergies. Of global importance are also animal dander, i.e. cat and dog dander, other pollens, such as mugwort pollens, and microfungi, such as Alternaria. On a regional basis yet other pollens may dominate, such as birch pollen in Northern and Central Europe, ragweed in the Eastern and Central United States, and Japanese cedar pollen in Japan. Insects, i.e. bee and wasp venoms, and foods each account for approximately 2% of all allergies.

Allergy, i.e. type I hyper-sensitivity, is caused by an inappropriate immunological reaction to foreign non-pathogenic substances. Important clinical manifestations of allergy include asthma, hay fever, eczema, and gastro intestinal disorders. The allergic reaction is prompt and peaks within 20 minutes upon contact with the offending allergen. Furthermore, the allergic reaction is specific in the sense that a particular individual is sensitised to particular allergen(s), whereas the individual does not necessarily show an allergic reaction to other substances known to cause allergic disease. The allergic phenotype is characterized by a pronounced inflammation of the mucosa of the target organ and by the presence of allergen specific antibody of the IgE class in the circulation and on the surfaced of mast-cells and basophils.

An allergic attack is initiated by the reaction of the foreign allergen with allergen specific IgE antibodies, when the antibodies are bound to high affinity IgE specific receptors on the surface of mast-cells and basophils. The mast-cells and basophils contain preformed mediators, i.e. histamine, tryptase, and other substances, which are released upon cross-linking of two or more receptor-bound IgE antibodies. IgE antibodies are cross-linked by the simultaneous binding of one allergen molecule. It therefore follows that a foreign substance having only one antibody binding epitope does not initiate an allergic reaction. The cross-linking of receptor bound IgE on the surface of mast-cells also leads to release of signaling molecules responsible for the attraction of eosinophils, allergen specific T-cells, and other types of cells to the site of the allergic response. These cells in interplay with allergen, IgE and effector cells, lead to a renewed flash of symptoms occurring 12-24 hours after allergen encounter (late phase reaction).

Allergy disease management comprises diagnosis and treatment including prophylactic treatments. Diagnosis of allergy is concerned with by the demonstration of allergen specific IgE and identification of the allergen source. In many cases a careful anamnesis may be sufficient for the diagnosis of allergy and for the identification of the offending allergen source material. Most often, however, the diagnosis is supported by objective measures, such as skin prick test, blood test, or provocation test.

The therapeutic options fall in three major categories. The first opportunity is allergen avoidance or reduction of the exposure. Whereas allergen avoidance is obvious e.g. in the case of food allergens, it may be difficult or expensive, as for house dust mite allergens, or it may be impossible, as for pollen allergens. The second and most widely used therapeutic option is the prescription of classical symptomatic drugs like anti-histamines and steroids. Symptomatic drugs are safe and efficient; however, they do not alter the natural cause of the disease, neither do they control the disease dissemination. The third therapeutic alternative is specific allergy vaccination that in most cases reduces or alleviates the allergic symptoms caused by the allergen in question.

Conventional specific allergy vaccination is a causal treatment for allergic disease. It interferes with basic immunological mechanisms resulting in persistent improvement of the patients' immune status. Thus, the protective effect of specific allergy vaccination extends beyond the treatment period in contrast to symptomatic drug treatment. Some patients receiving the treatment are cured, and in addition, most patients experience a relief in disease severity and symptoms experienced, or at least an arrest in disease aggravation. Thus, specific allergy vaccination has preventive effects reducing the risk of hay fever developing into asthma, and reducing the risk of developing new sensitivities.

The immunological mechanism underlying successful allergy vaccination is not known in detail. A specific immune response, such as the production of antibodies against a particular pathogen, is known as an adaptive immune response. This response can be distinguished from the innate immune response, which is an unspecific reaction towards pathogens. An allergy vaccine is bound to address the adaptive immune response, which includes cells and molecules with antigen specificity, such as T-cells and the antibody producing B-cells. B-cells cannot mature into antibody producing cells without help from T-cells of the corresponding specificity. T-cells that participate in the stimulation of allergic immune responses are primarily of the Th2 type. Establishment of a new balance between Th1 and Th2 cells has been proposed to be beneficial and central to the immunological mechanism of specific allergy vaccination. Whether this is brought about by a reduction in Th2 cells, a shift from Th2 to Th1 cells, or an up-regulation of Th1 cells is controversial. Recently, regulatory T-cells have been proposed to be important for the mechanism of allergy vaccination. According to this model regulatory T-cells, i.e. Th3 or Tr1 cells, down-regulate both Th1 and Th2 cells of the corresponding antigen specificity. In spite of these ambiguities it is generally believed that an active vaccine must have the capacity to stimulate allergen specific T-cells, preferably TH1 cells.

Specific allergy vaccination (SAV), formerly known as Specific Immunotheraphy or Hyposensitization, has been used for the treatment of Type 1 IgE mediated allergic disease since the beginning of this century.

The general benefits obtained through SAV are: a) reduction of allergic symptoms and medicine consumption, b) improved tolerance towards the allergens in the eyes, nose and lungs and c) reduced skin reactivity (early and late phase reactions).

The basic mechanism behind the improvement obtained by SAV is unknown, but a number of common features can be extracted from the numerous SAV studies performed in the last decades: 1) the amount of total IgE is unchanged during the treatment period, 2) the amount of allergen specific IgE increases transiently during updosing, then it falls back to the initial (pretreatment) level, 3) the epitope specificity and affinity of IgE remains unchanged, 4) allergen specific IgG, in particularly IgG4, raises sharply during SAV, 5) a new Th0/1/Reg response is apparently initiated and 6) the Th2 response seem unchanged. There is no correlation between the effect induced by SAV and the onset of specific IgG.

SAV induces a new immune response which matures during the treatment period (Th0/1 T-cells are recruited, an allergen specific IgX (X may be A1, A2, G1, G2, G3, G4, M or D) is initiated). As the affinity (or amount/affinity) of the new antibody response, IgX, has matured, IgX may compete efficiently with IgE for the allergen(s), inhibiting the "normal" Th2 based allergic response characterised by the cross-linking of receptor bound IgE on the surface of mast-cells and basophils. Hence, clinical symptoms will gradually be reduced.

Specific allergy vaccination is, in spite of its virtues, not in widespread use, primarily for two reasons. One reason is the inconveniences associated with the traditional vaccination programme that comprises repeated vaccinations i.a. injections over a several months. The other reason is, more importantly, the risk of allergic side reactions. Ordinary vaccinations against infectious agents are efficiently performed using a single or a few high dose immunizations. This strategy, however, cannot be used for allergy vaccination since a pathological immune response is already ongoing.

Conventional specific allergy vaccination is therefore carried out using multiple subcutaneous immunizations applied over an extended time period. The course is divided in two phases, the up dosing and the maintenance phase. In the up dosing phase increasing doses are applied, typically over a 16-week period, starting with minute doses. When the recommended maintenance dose is reached, this dose is applied for the maintenance phase, typically with injections every six weeks. Following each injection the patient must remain under medical attendance for 30 minutes due to the risk of anaphylactic side reactions, which in principle although extremely rare could be life-threatening. In addition; the clinic should be equipped to support emergency treatment.

There is no doubt that a vaccine based on a different route of administration would eliminate or reduce the risk for allergic side reactions inherent in the current subcutaneous based vaccine as well as would facilitate a more widespread use, possibly even enabling self vaccination at home.

Attempts to improve vaccines for specific allergy vaccination have been performed for over 30 years and include multifarious approaches. Several approaches have addressed the allergen itself through modification of the IgE reactivity.

Allergen extracts purified from grass pollen, tree pollen and house dust mites have been used as pharmaceuticals for many years without any acknowledged problems with toxicity.

SUMMARY OF THE INVENTION

The present invention relates to a process for producing an allergen extract from a biological allergen source material comprising the steps of a) contacting the source material with a liquid extraction agent to produce a allergen extract mixture containing allergens dissolved in a liquid phase and a solid phase consisting of source material residues, b) subjecting the allergen extract mixture to a first separation step to remove the solid phase to produce a crude allergen extract, c) subjecting the crude allergen extract to a low molecular fraction removal step to remove molecules having a molecular size of less than 10 kDa, and d) carrying out step c) until the allergen extract has conductivity of below 2000 µS/cm at 25° C. to obtain a purified allergen extract.

Recent research has surprisingly shown that some types of allergen extracts from biological allergen source materials, e.g. extracts from grass pollen, which has hitherto been believed to contain no toxic components, in fact contains components, which in at least some toxicity tests results in the tests being positive. The present invention is based on the recognition of this technical problem. This finding is surprising, since such extracts have been used for many years without any knowledge of or experimental findings to this effect. Also, it is surprising, since the biological source materials, from which the extracts are obtained, are biological materials, which in general are believed to be harmless and non-toxic by nature, and for example also serves as feed for various animals.

The present invention is based on the surprising finding that when using the process, all toxic components of the allergen extract is removed as evidences by appropriate toxicity testing of the purified allergen extract. It is believed that the essential step for obtaining the removal of toxic components is the step of removing the low molecular fraction of the allergen extract to a certain level of purity as expressed by the conductivity of the purified allergen extract. The conductivity of the purified allergen extract expresses the level to which the low molecular fraction has been removed, since the low molecular fraction removed comprises small molecules having a maximum molecular size of 10 kDa, as well as salts and ions. Accordingly, the present invention is based on the first recognition that the toxic component is present in the low molecular fraction of the allergen extract. Secondly, the invention is based on the recognition that in order to obtain a sufficient removal of toxic components it is necessary to remove the low molecular fraction of the allergen extract to a high level of purity.

An additional advantage of the process of the invention is that the low content of salts and ions of the purified allergen extract enables subsequent processing of the extract, e.g. freeze drying, freezing and storage of the frozen extract to be conducted at a higher temperature, because the depression of the freezing point caused by the salts and ions are eliminated or reduced. Also, problems due to precipitation of salts during the subsequent processing are avoided.

DETAILED DESCRIPTION OF THE INVENTION

Allergen Extract

The allergen extract according to the present invention may be an extract of a biological allergen source material containing any naturally occurring protein allergen that has been reported to induce allergic, i.e. IgE mediated, reactions upon their repeated exposure to an individual. Examples of naturally occurring allergens include pollen allergens (tree-, herb, weed-, and grass pollen allergens), insect allergens (inhalant, saliva and venom allergens, e.g. mite allergens, cockroach and midges allergens, hymenopthera venom allergens), animal hair and dandruff allergens (from e.g. dog, cat, horse, rat, mouse etc.), and food allergens. Important pollen allergens from trees, grasses and herbs are such originating from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.a. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*. Other important inhalation allergens are those from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi and moulds are i.a. such originating from the genera *Alternaria* and *Cladosporium*.

In a particular embodiment of the invention the allergen is selected from the group consisting of Bet v 1, Aln g 1, Cor a 1, Car b 1, Que a 1, Cry j 1, Cry j 2, Cup a 1, Cup s 1, Jun a 1, Jun a 2, Jun a 3, Ole e 1, Lig v 1, Pla l 1, Pla a 2, Amb a 1, Amb a 2, Amb t 5, Art v 1, Art v 2 Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phi p 1, Phi p 5, Phi p 6, Poa p 1, Poa p 5, Sec c 1, Sec c 5, Sor h 1, Der f 1, Der f 2, Der p 1, Der p 2, Der p 7, Der m 1, Eur m 2, Gly d 1, Lep d 2, Blo t 1, Tyr p 2, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dil m 2, Dol m 5, Pol a 1, Pol a 2, Pol a 5, Sol i 1, Sol i 2, Sol i 3 and Sol i 4, Alt a 1, Cla h 1, Asp f 1, Bos d 4, Mal d 1, Gly m 1, Gly m 2, Gly m 3, Ara h 1, Ara h 2, Ara h 3, Ara h 4 and Ara h 5.

In a preferred embodiment of the invention the allergen is selected from the group consisting of a tree pollen allergen, a grass pollen allergen, a house dust mite allergen, a storage mite allergen, a weed allergen, a mould allergen, a cat allergen and a dog allergen.

Steps of the Process of the Invention

The steps of a process for extracting and purifying an allergen extract from a biological allergen source material depend on the type of the source material, as the nature of various source materials, such as grass pollen, tree pollen and house dust mite residues, differs significantly. Typical steps include an extraction step, a separation step to remove the solid residues of the source material, and purification of the allergen extract.

The liquid extraction agent may e.g. be water or an aqueous buffer. The extraction step is carried out by mixing a liquid extraction agent with a biological allergen source material to form a suspension of the solid phase source material in the liquid phase of extraction agent, and the mixture is agitated. The extraction is preferably continued for a selected period of time of e.g. from 1 to 24 hours, preferably from 2 to 12 hours, during which the temperature is adjusted to e.g. from 2 to 25° C., preferably from 3 to 15° C., and the pH is adjusted to from 5 to 9, preferably from 6 to 8. At the end of the extraction an allergen extract mixture is obtained, which comprises a solid phase composed of the source material residues, e.g. the solid matter remaining from the extraction, and a liquid phase containing the molecules extracted from the source material.

The allergen extract mixture is then subjected to a separation step, wherein at least most of the source material residues, in particular the larger particles thereof, is removed. This separation may be carried out e.g. by centrifugation or filtration. The removal of the source material residues results in a crude allergen extract, which contains the extracted molecules in solution and to a certain extent smaller particles, depending on the separation method and equipment used.

Optionally, the crude allergen extract may then be concentrated e.g. by ultrafiltration, precipitation and/or ion exchange chromatography.

The crude allergen extract is then subjected to a low molecular fraction removal step, which may be carried out e.g. by means of ultrafiltration, diafiltration, dialysis and/or gel filtration. In the low molecular fraction removal step, molecules having a molecular size of less than 10 kDa are removed. In an alternative embodiment, molecules having a molecular size of less than 5 kDa, are removed. In yet an alternative embodiment, molecules having a molecular size of less than 3 kDa, are removed.

The low molecular fraction removal step is continued until the conductivity is less than 2000 µS/cm at 25° C. (aqueous solvent). This is accomplished by measuring the conductivity continuously and using this measurement as a basis for controlling the low molecular fraction removal step. Preferably, the low molecular fraction removal step is continued until the conductivity is less than 1500 µS/cm at 25° C., more preferably less than 1200 µS/cm at 25° C., more preferably less than 1000 µS/cm at 25° C., more preferably less than 900 µS/cm at 25° C., more preferably between 200 and 800 µS/cm at 25° C., and most preferably between 300 and 700 µS/cm at 25° C. (aqueous solvent).

When diafiltration is used in the low molecular fraction removal step, the process is preferably carried out using a volume of solvent of between 1 and 12, preferably from 2 to 11, preferably from 3 to 10, preferably from 4 to 9, preferably from 5 to 8, and most preferably from 6 to 7, relative to the volume of the volume of the crude allergen extract purified.

Optionally, the purified allergen extract may then be concentrated once more e.g. by ultrafiltration, precipitation and/or ion exchange chromatography.

Toxicity Test

The purified allergen extract produced by the process of the invention may be tested for a potential content of a toxic component.

The toxicity test used for such testing may be any conventional toxicity test, which is relevant for testing an active substance in the form of an allergen extract, including pre-clinical tests and clinical tests.

Conventional toxicity tests include i.a. any test approved by ICH (International Conference on Harmonisation of technical requirements for registration of pharmaceutical for human use) as well as any conventional endotoxin test. Pre-clinical toxicity tests include in vivo and in vitro tests. Categories of pre-clinical toxicity tests include (referring to ICH itemisation) S1) Carcinogenicity Studies, S2) Genotoxicity Studies, S3) Toxicokinetics and Pharmacokinetics, S4) Toxicity Testing, S5) Reproductive Toxicology, S6) Biotechnology Products, S7) Pharmacology Studies, S8) Immunotoxicology Studies, and M3) Joint Safety/Efficacy Topic. Reference is made to the ICH guidelines as in force on the filing date of this patent application.

Genotoxicity tests include i) a test for gene mutation in bacteria, e.g. an Ames test, (ii) an in vitro test with cytogenetic evaluation of chromosomal damage with mammalian cells, (iii) an in vitro mouse lymphoma tk assay, and (iv) an in vivo test for chromosomal damage using rodent hematopoietic cells.

Conventional endotoxin tests include the Limulus Amoebucyte Lysate (LAL) in vitro test and the rabbit fever in vivo test.

DEFINITIONS

In connection with the present invention, the following terms are defined as follows:

The term "ultrafiltration" means up-concentration of a solution in a membrane filter, i.e. the permeate of the solution is discarded and the retentate of the solution may be used or recycled and subjected to another filtration. The recycling may be continued until a desired concentration of the solution is achieved.

The term "diafiltration" means filtration of a solution in a membrane filter while maintaining the same volume of the solution, i.e. the permeate of the solution is discarded and a volume of solvent, e.g. water, is added to the retentate of the solution, which may be used or recycled and subjected to another filtration. This may be continued until the desired concentration of the solution is achieved.

The term "dialysis" means removal of dissolved components by osmosis from a solution, e.g. by filling the solution into perforated tubes, which are then placed in a container filled with solvent and left to stand for a period of time, during which the dissolved components by osmosis diffuse out of the tubes into the surrounding solvent.

The expression "toxic component" means any component, which is positive in any conventional toxicity test, including those mentioned by ICH (International Conference on Harmonisation of technical requirements for registration of pharmaceutical for human use) on the date of filing of this application, or an endotoxin test.

The expression "endotoxin test" means any conventional endotoxin test.

The term "endotoxin" means a poisonous substance present in or originating from a microorganism.

EXAMPLE

Extraction and Purification of Grass Pollen

The process consists of extraction of the allergenic source material (grass pollen) followed by removal of the grass pollen by depth filter filtration, concentration by cross-flow ultrafiltration and removal of salts and small molecules by cross-flow diafiltration. Then the extract is further concentrated by ultra-filtration and the amount of dry weight per ml is adjusted. After clarification through a depth filter and a membrane filter the diafiltrated extract is freeze-dried or subjected to freezing and stored until the time of its use as a starting material for the manufacture of a vaccine formulation.

Extraction

The source material is mixed with extraction buffer in ratio 1:10 (sodium chloride 0.9%, sodium hydrogen carbonate 0.1%, purified water or higher water quality) and agitated at 8° C. for 2 hours. The pH is adjusted to 7.5 during the extraction.

Dead End Filtration

After the extraction step filter-aid is added to the extraction mixture and the solution is filtered by depth filter filtration in order to remove pollens and other particulate matter from the extract. The filter is then flushed using purified water (or higher water quality). Then the extract is filtered through a 0.45 μm membrane for clarification.

First Concentration, Dia-Filtration and 2nd Concentration.

The extract is concentrated by ultrafiltration on a 5 kDa membrane. After the concentration step, small molecules and salts are removed from the extract by diafiltration against purified water (or higher water quality), again by using the 5 kDa membrane. The diafiltration continues until the conductivity is 500 μS/cm, 25° C. After diafiltration the solution is further concentrated.

Dry Weight Adjustment

The dry weight concentration is adjusted to 50 mg/ml by adding purified water (or higher water quality).

Holding Time

After the dry weight adjustment the extract can be stored at 5° C. for 24 h until further processing.

Clarification by Filtration

Before stabilisation by freezing prior to storage the extract is filtered through a depth filter and a 0.2 μm filter for clarification.

Toxicity Test

An allergen extract produced using the process described above was subjected to an Ames test (a genotoxicity test), and the result of the Ames test was negative.

The invention claimed is

1. A process for producing an allergen extract from a biological allergen source material selected from the group consisting of pollen from birch trees, weeds, herbs and grass comprising the steps of
   a) contacting the source material with an aqueous extraction agent to produce an allergen extract mixture containing allergens dissolved in a liquid phase and a solid phase consisting of source material residues,
   b) subjecting the allergen extract mixture to a first separation step to remove the solid phase to produce a crude allergen extract,
   c) subjecting the crude allergen extract to a low molecular fraction removal step to remove molecules having a molecular size of less than 10 kDa, said low molecular fraction removal step being selected from the group consisting of an ultrafiltration step, a diafiltration step and a dialysis step, and
   d) carrying out step c) while measuring the conductivity continuously until the allergen extract has conductivity of less than 900 μS/cm at 25° C. to obtain a purified allergen extract.

2. A process according to claim 1, wherein in step c) molecules having a molecular size of less than 5 kDa are removed.

3. A process according to claim 2, wherein in step c) molecules having a molecular size of less than 3 kDa are removed.

4. A process according to claim 1, wherein the low molecular fraction removal step is an ultrafiltration step.

5. A process according to claim 1, wherein the low molecular fraction removal step is a diafiltration step.

6. A process according to claim 1, wherein the low molecular fraction removal step is a dialysis step.

7. A process according to claim 1, wherein the first separation step is filtration.

8. A process according to claim 1, wherein the low molecular fraction removal step is continued until the conductivity is between 200 and 800 µS/cm at 25° C.

9. A process according to claim 8, wherein the low molecular fraction removal step is continued until the conductivity is between 300 and 700 µS/cm at 25° C.

10. A process for producing an allergen extract from a biological allergen source material selected from the group consisting of pollen from birch trees, weeds, herbs and grass comprising the steps of
   a) contacting the source material with an aqueous extraction agent to produce an allergen extract mixture containing allergens dissolved in a liquid phase and a solid phase consisting of source material residues,
   b) subjecting the allergen extract mixture to a first separation step to remove the solid phase to produce a crude allergen extract,
   c) subjecting the crude allergen extract to a low molecular fraction removal step to remove molecules having a molecular size of less than 10 kDa, wherein said low molecular fraction removal step comprises at least one member selected from the group consisting of an ultrafiltration step, a diafiltration step and a dialysis step, and
   d) carrying out step c) until the allergen extract has conductivity of below 2000 µS/cm at 25° C. to obtain a purified allergen extract.

11. The process according to claim 10, wherein in step c) molecules having a molecular size of less than 5 kDa are removed.

12. The process according to claim 11, wherein in step c) molecules having a molecular size of less than 3 kDa are removed.

13. A process for producing an allergen extract from a biological allergen source material which comprises grass pollen comprising the steps of
   a) contacting the source material with an aqueous extraction agent to produce an allergen extract mixture containing allergens dissolved in a liquid phase and a solid phase consisting of source material residues,
   b) subjecting the allergen extract mixture to a first separation step to remove the solid phase to produce a crude allergen extract,
   c) subjecting the crude allergen extract to a low molecular fraction removal step to remove molecules having a molecular size of less than 10 kDa, and
   d) carrying out step c) until the allergen extract has conductivity of below 2000 µS/cm at 25° C. to obtain a purified allergen extract.

14. The process according to claim 13, wherein said low molecular fraction removal step comprises at least one member selected from the group consisting of ultrafiltration, diafiltration and dialysis.

15. The process according to claim 14, wherein in step c) molecules having a molecular size of less than 5 kDa are removed.

16. The process according to claim 15, wherein in step c) molecules having a molecular size of less than 3 kDa are removed.

* * * * *